United States Patent
Di Lullo et al.

(10) Patent No.: US 7,240,537 B2
(45) Date of Patent: Jul. 10, 2007

(54) METHOD FOR THE DETERMINATION OF THE WALL FRICTION PROFILE ALONG PIPES BY PRESSURE TRANSIENTS MEASUREMENTS

(75) Inventors: Alberto Di Lullo, Sirmione (IT); Sebastiano Correra, San Donato Milanese (IT); Vittorio Rota, San Donato Milanese (IT); Gilberto Toffolo, San Foca (IT); Martin Bartosek, Legnano (IT)

(73) Assignees: ENI S.p.A., Rome (IT); Enitechnologie S.p.A., San Donato Milanese (IT)

( * ) Notice: Subject to any disclaimer, the term of this patent is extended or adjusted under 35 U.S.C. 154(b) by 519 days.

(21) Appl. No.: 10/484,808

(22) PCT Filed: Jul. 30, 2002

(86) PCT No.: PCT/EP02/08547

§ 371 (c)(1),
(2), (4) Date: Jul. 13, 2004

(87) PCT Pub. No.: WO03/012401

PCT Pub. Date: Feb. 13, 2003

(65) Prior Publication Data

US 2004/0261505 A1 Dec. 30, 2004

(30) Foreign Application Priority Data

Aug. 2, 2001 (IT) .......................... MI2001A1689
Mar. 27, 2002 (IT) .......................... MI2002A0634

(51) Int. Cl.
*G01M 3/04* (2006.01)

(52) U.S. Cl. ....................................................... 73/49.5
(58) Field of Classification Search ................. 73/49.5
See application file for complete search history.

(56) References Cited

U.S. PATENT DOCUMENTS

| | | | | |
|---|---|---|---|---|
| 2,929,248 A * | 3/1960 | Sprenkle | ....................... | 73/198 |
| 3,374,341 A * | 3/1968 | Klotz | ....................... | 700/301 |
| 3,410,479 A | 11/1968 | Carl-Goran | | |
| 4,419,892 A | 12/1983 | Goolsby et al. | | |
| 4,521,864 A | 6/1985 | Characklis | | |
| 4,545,259 A * | 10/1985 | Jensen et al. | ............. | 73/861.28 |
| 4,677,849 A * | 7/1987 | Ayoub et al. | ............. | 73/152.37 |
| 4,726,219 A * | 2/1988 | Pearson et al. | ............. | 73/54.04 |
| 5,467,650 A * | 11/1995 | Cushing | ....................... | 73/215 |
| 6,253,624 B1 * | 7/2001 | Broden et al. | ........... | 73/861.44 |
| 6,993,963 B1 * | 2/2006 | Gudmundsson | .......... | 73/152.52 |
| 2005/0279532 A1 * | 12/2005 | Ballantyne et al. | ........... | 175/40 |
| 2006/0272417 A1 * | 12/2006 | Zanker et al. | ................ | 73/592 |

FOREIGN PATENT DOCUMENTS

WO 99 64781 12/1999

* cited by examiner

*Primary Examiner*—Hezron Williams
*Assistant Examiner*—John Fitzgerald
(74) *Attorney, Agent, or Firm*—Oblon, Spivak, McClelland, Maier & Neustadt, P.C.

(57) ABSTRACT

The present invention deals with a method which allows to determine the wall friction profile along pipes transporting liquids, particularly petroleum industry liquids, by measuring the pressure transients induced by fast changes in the flow rate. This method is applicable to pipes in which the discharge pressure is greater then the bubble point of the transported liquid and, in any case, when free gas is absent in the pipe.

7 Claims, 6 Drawing Sheets

Comparison of the wall friction pressure drop profile before and after a solvent wash of the tube.

Comparison of the wall friction pressure drops calculated before and after a solvent wash.

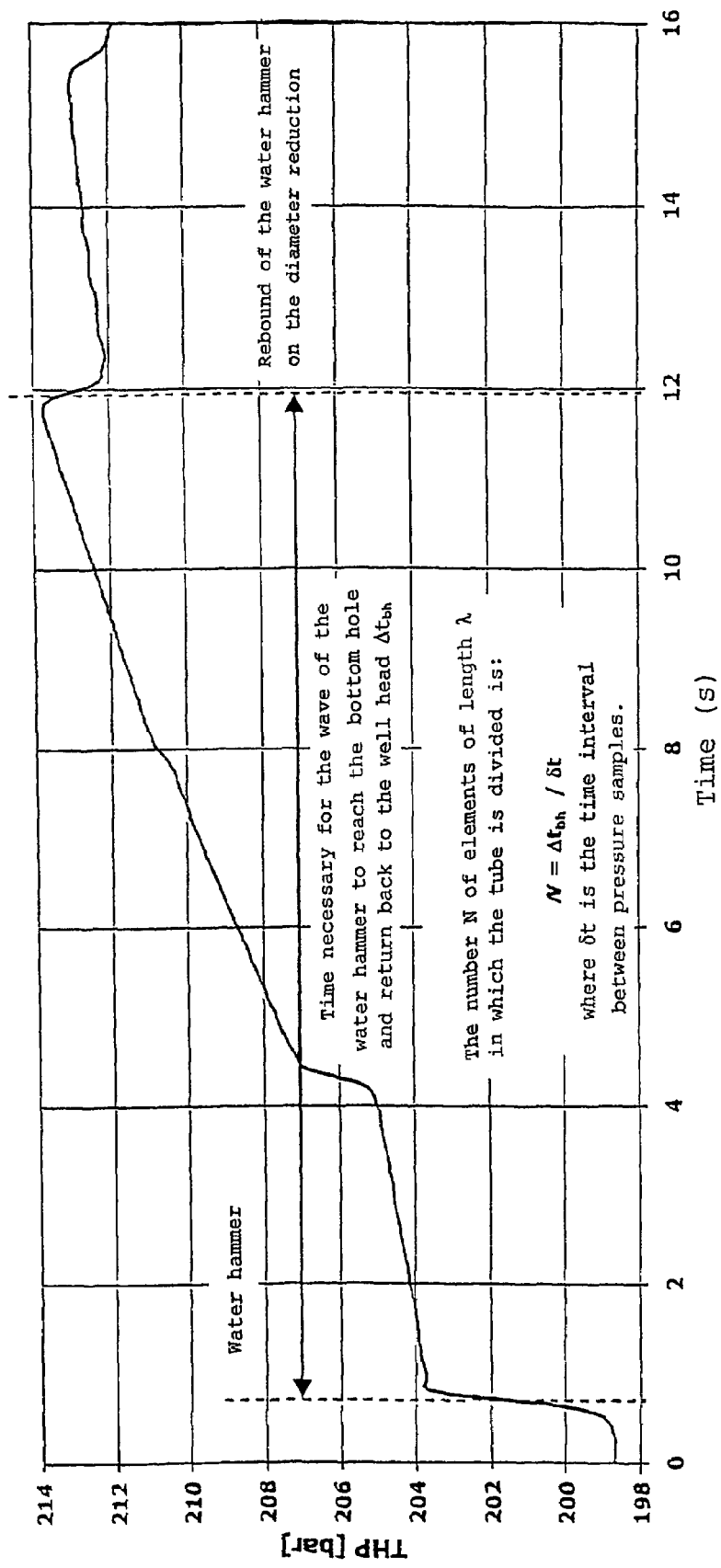
Figure 1: THP curve as a function of time.

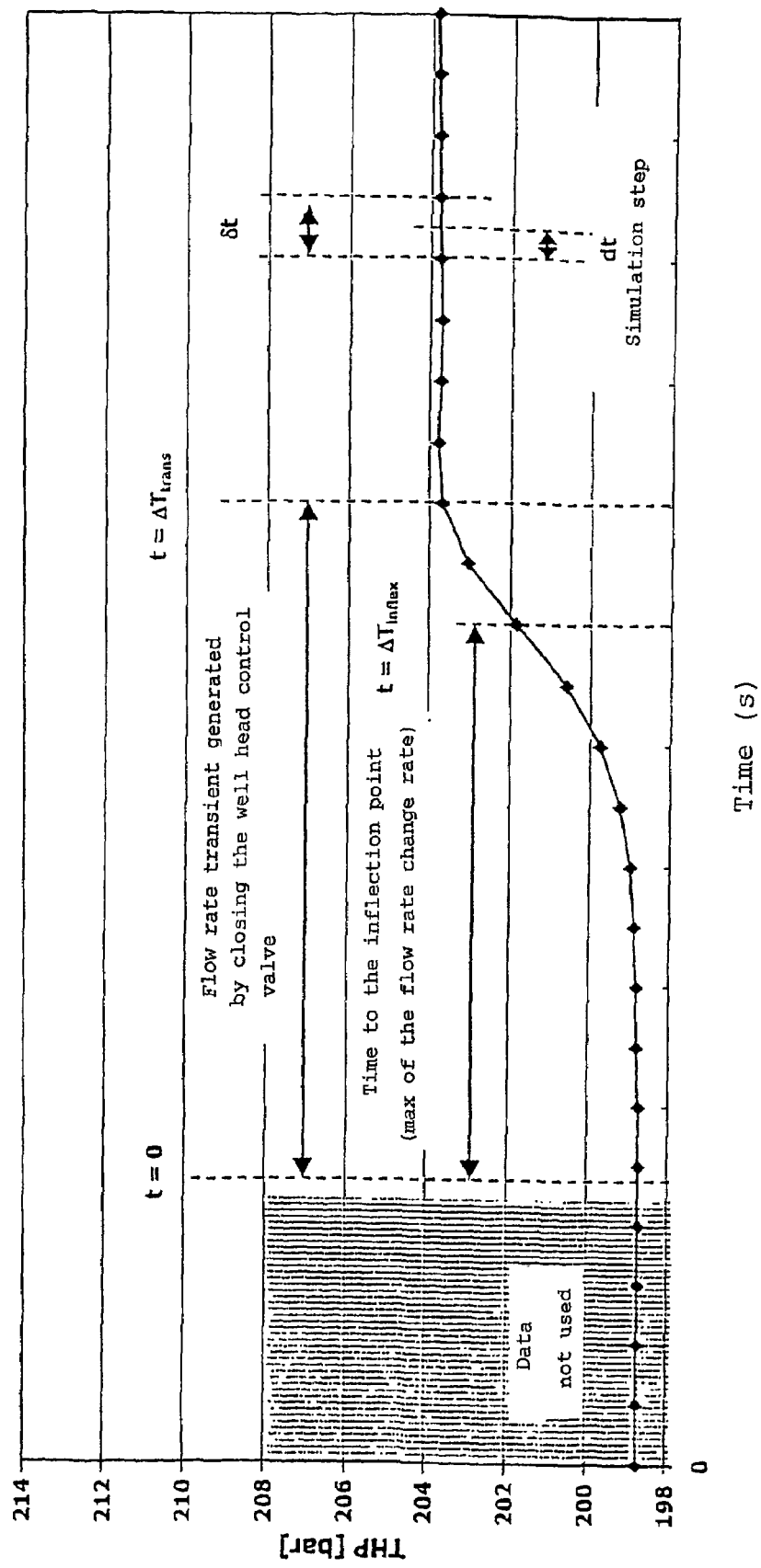
Figure 2: Definition of different times

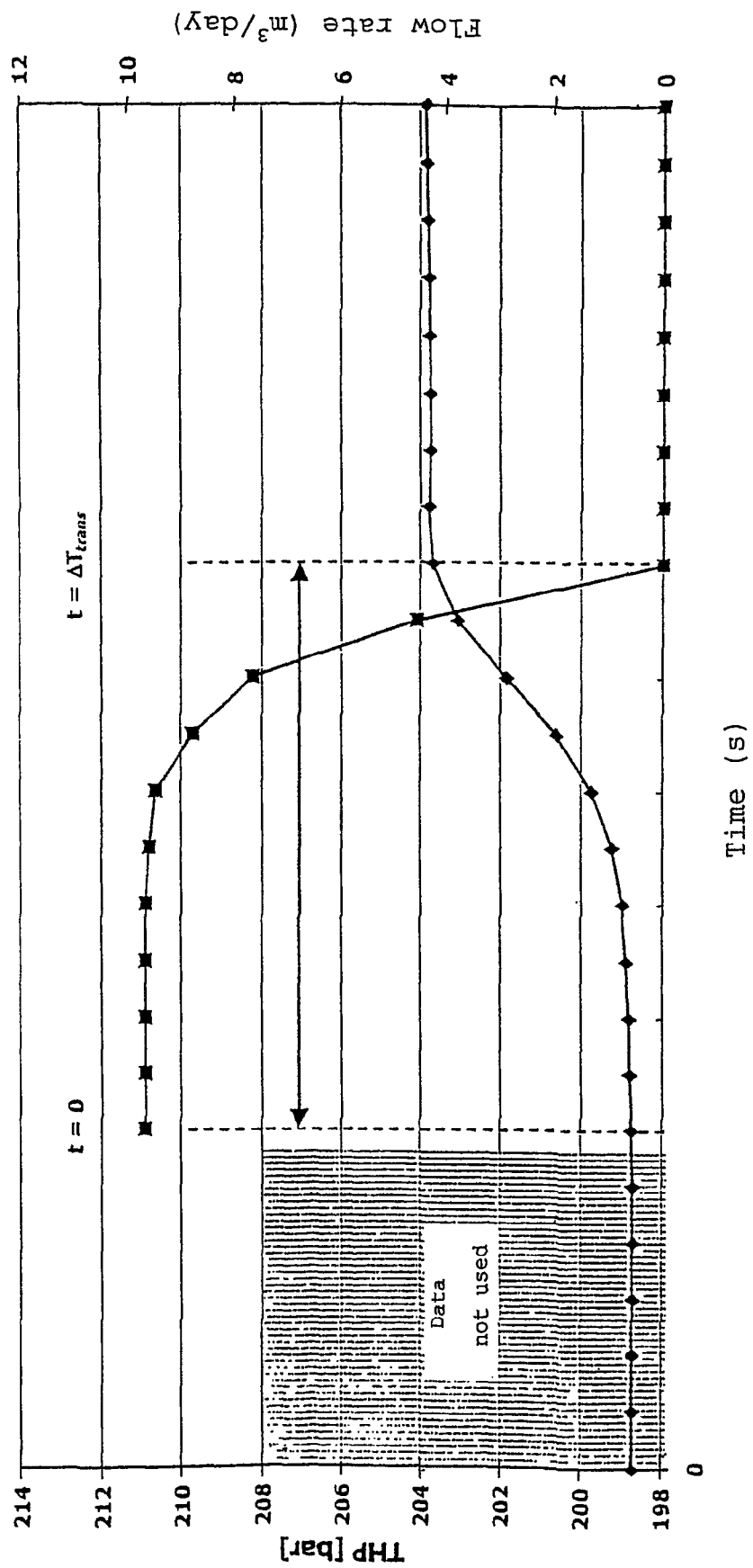
Figure 3: Interpolated evolution of the flow rate transients.

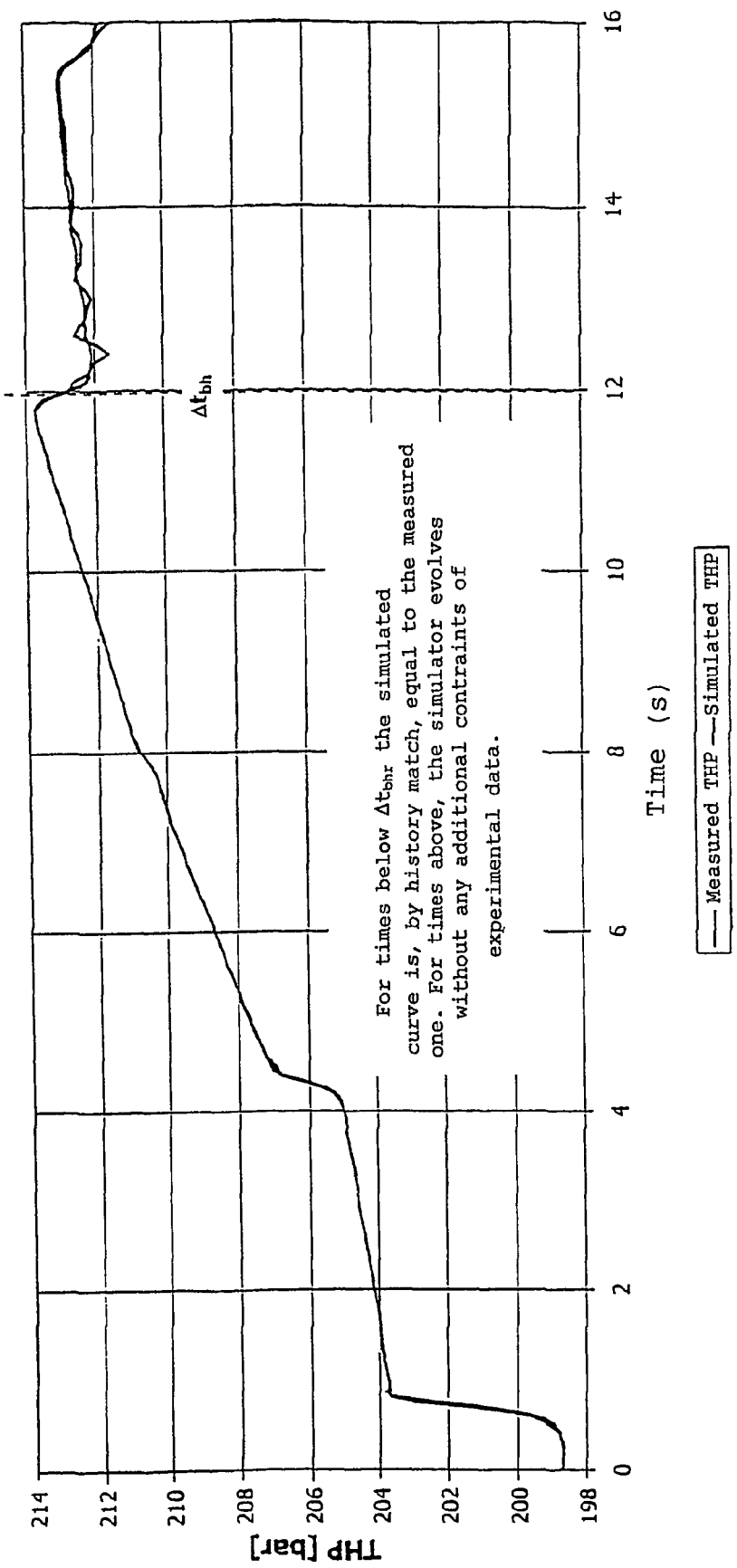
Figure 4: Comparison between the measured values and the calculated values with the simulator.

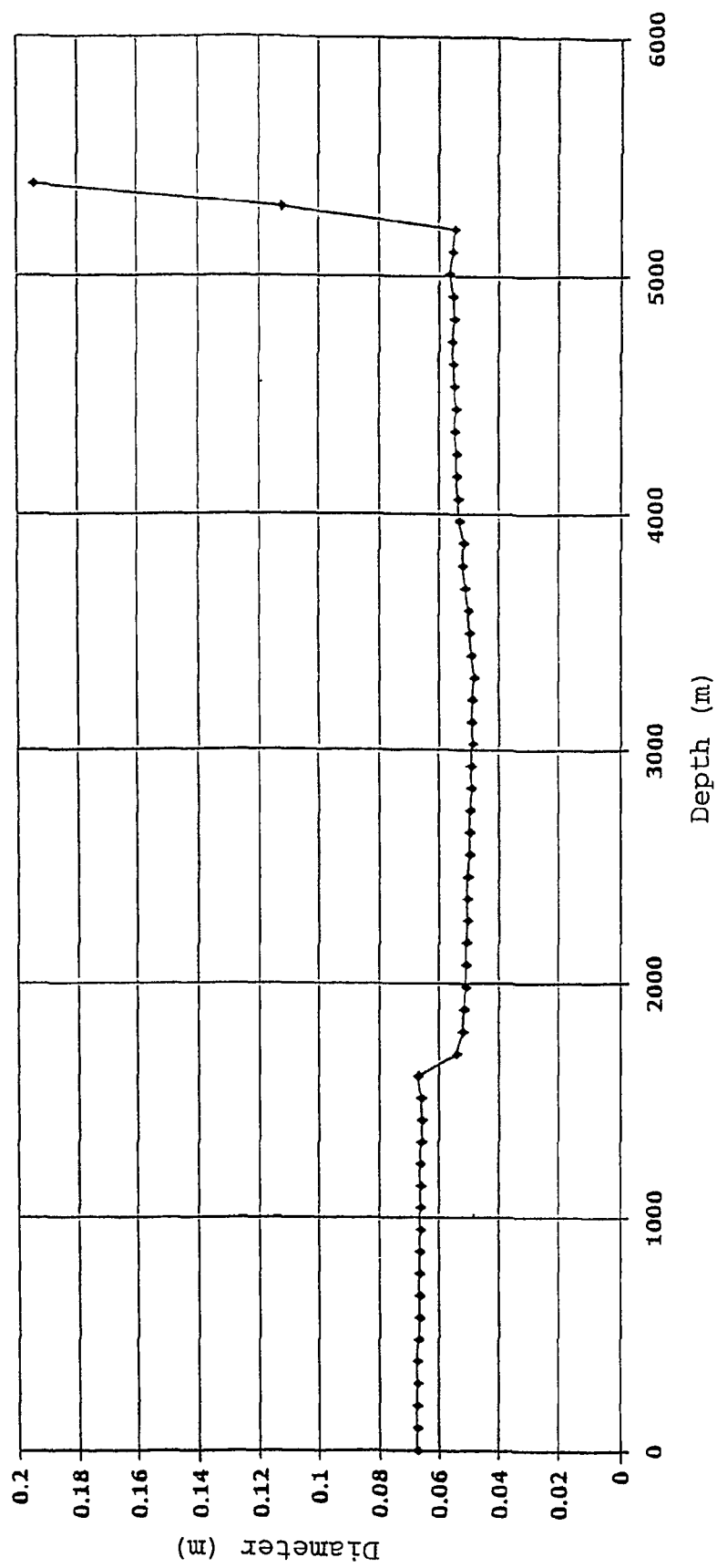
Figure 5: Profile of the diameters calculated as a function of depth.

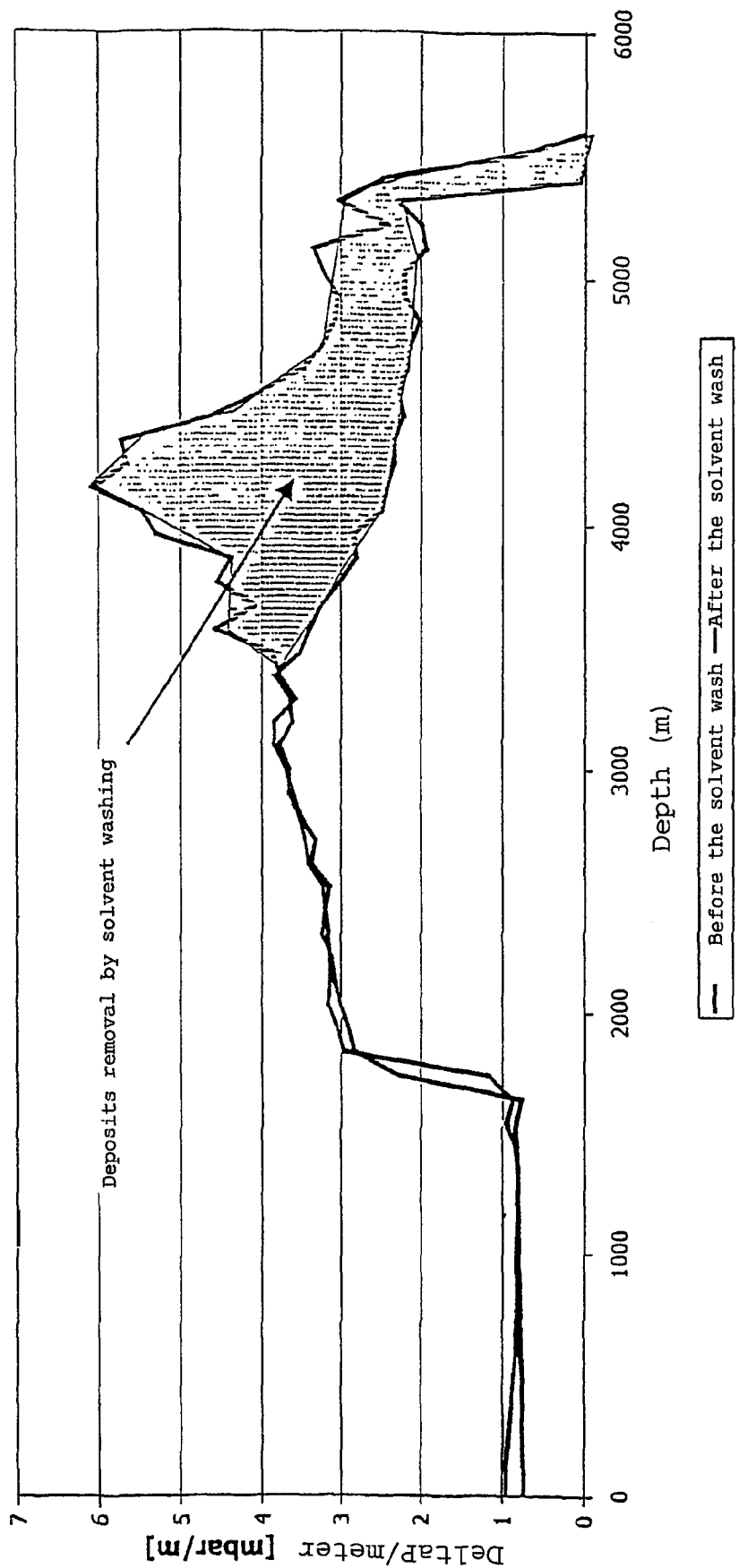
Figure 6: Comparison of the wall friction pressure drops calculated before and after a solvent wash.

METHOD FOR THE DETERMINATION OF THE WALL FRICTION PROFILE ALONG PIPES BY PRESSURE TRANSIENTS MEASUREMENTS

The present inventions deals with a method which allows to determine the wall friction profile along pipes transporting liquids, particularly petroleum industry liquids.

In petroleum production, the crude is extracted from the reservoir through a production pipeline, starting from the reservoir and arriving at the surface. On the surface, a system of control valves can be found, possibly together with facilities for the separation of reservoir water and associated natural gas and, in many cases, a pipeline system for oil transportation.

During production, deposits may form in the pipes, with the effect of increasing pressure losses and hindering production and transport.

The method of the present invention allows to determine the wall friction profile along the pipes by measuring and analyzing the pressure transients induced by fast changes in the flow rate. This method allows to localize, in a non-destructive and non-intrusive way, the pipe sections where deposits, roughness changes or restrictions of any kind occur.

The method of the present invention is applicable to any pipe transporting liquids. In particular, the method can be applied when the discharge pressure is greater than the bubble point ($P_b$) of the transported liquid and, in any case, when free gas is essentially absent in the pipe. For the application of this method it is not necessary to measure the liquid flow rate. Moreover, the pipe may be horizontal, vertical or laid along any vertical profile.

The present invention deals with a method for the determination of the wall friction profile in any pipe transporting liquids, particularly petroleum industry liquids, applicable when the discharge pressure of the pipe is greater than the bubble pressure of the transported liquids, consisting in:

1) a first stage of generation and measurement along time of pressure transients induced by fast flow rate changes, preferably obtained by closing rapidly and completely a valve placed at one end of the pipe itself.
2) a second stage of interpolation of the pressure data obtained at Stage 1, thus obtaining the evolution of flow rate during the transients
3) a third stage of processing of the pressure data obtained at Stage 1 by which, using the flow rate evolution determined at Stage 2, the diameter or roughness profile along the pipe is computed
4) a fourth and last stage in which the diameter or roughness profile obtained at Stage 3 is used to compute the pressure drop profile at any specified constant flow rate.

The use of a specified constant flow rate at Stage 4 allows the comparison of pressure drop profile obtained in different operating conditions.

The spatial resolution of the wall friction profile along the pipe, obtained by applying the present invention, depends on both the flow rate transient and the sampling frequency of the pressure data. In general, the best results are obtained for flow rate transient fully completed in less than 0.5 s and sampling frequencies greater than 20 Hz. The relationship between the above two parameters and spatial resolution will be clarified later in the document.

For the data processing to be performed at Stages 2, 3 and 4, it is necessary to have a numerical simulator with adequate capabilities. So, before describing the method itself, a description of a suitable simulator is reported. For the sake of clarity, in the description of the simulator we will refer to the case of a petroleum well.

The same concepts are applicable to any other pipe.

The simulator is necessary for a correct analysis of the pressure data and must be capable of simulating the evolution of the "shock" wave induced by the flow rate change generated at one end of the pipe, e.g. at the well head.

The equations used by the simulator are the following:

$$\frac{\partial p}{\partial t} + \rho c^2 \frac{\partial v}{\partial x} \tag{1}$$

$$\rho \frac{\partial v}{\partial t} + \frac{\partial p}{\partial x} = -\phi(V, D) \tag{2}$$

$$\phi(V, D) = \frac{\lambda(\text{Re})}{D} + \rho \frac{V|V|}{2} \tag{3}$$

$$\text{Re} = \frac{|V| D \rho}{\mu} \tag{4}$$

$$p = p(t,x) + \rho g x \tag{5}$$

where the pressure $p(t,x)$ is the difference between the pressure at position x and time t and the hydrostatic pressure at x:

$$p(t,x) = P_{real}(t,x) - \rho g z(x) \tag{6}$$

and

D is the pipe diameter x is the distance along the pipe from the point where the flow rate transient is generated (e.g. the location of the valve)

z(x) is the vertical depth of the pipe at x

Re is Reynolds number, defined in eq. (4)

c is the speed of propagation of the pressure transient in the pipe;

f is the Fanning friction factor g is the gravity acceleration t is time v(x,t) is the fluid's velocity at x and t $\mu$ is the fluid's viscosity $\rho$ is the fluid's density $\phi$ is a quantity defined in eq. (3)

With THP (tube head pressure) we will briefly indicate the pressure measured where the transient is generated: $p(x=0, t)$.

For the numerical solution of the equations, the pipe is divided into a number of elements $E_n$, n=1 ... N, each constituted by two halves of equal length but, possibly, different diameter D and roughness $\epsilon$:

$$D^{up}_n \text{ and } D^{down}_n$$

$$\epsilon^{up}_n \text{ e } \epsilon^{down}_n$$

where the values denoted with up and down are respectively closer and farther form the origin x=0.

Each element $E_n$ has length: $\lambda = \delta t \, c/2$, where $\delta t$ is the time interval between pressure samples, and is located at a distance $x_n = n\lambda - \lambda/2$ from the origin and at a depth $z_n = z_n(x_n)$. Any change in diameter or roughness occurs only within each element, so that the values for the down part of each element are equal to those of the up part of the following one, and so on:

$$D^{down}_n = D^{up}_{n+1}$$

$$\epsilon^{down}_n = \epsilon^{up}_{n+1}$$

The total number N of elements is given by:

$$N = \Delta t_{flight}/\delta t$$

where $\Delta t_{flight}$ is the time necessary for the pressure transient to travel from one end of the tube to the other, e.g. from the well head to the well bottom, as shown in FIG. 1.

In the elements where the upper diameter is different from the lower diameter, the following equation is applied:

$$v^{up}_n \pi (D^{up}_n)^2/4 = v^{down}_n \pi (D^{down}_n)^2/4$$

which expresses the mass balance in the element.

The initial conditions for the solution of the system of differential equations above are represented by the pressure profile along the pipe under steady conditions, which is computed for each element in the pipe, starting from the end where the initial pressure is known, applying the Navier-Stokes equation for the pressure losses and an empirical correlation for the estimation of the friction factor, like e.g. Colebrook formula (Colebrook, *J. Inst. Civ. Eng. [London]*, 11,133-156 1938-39).

The boundary conditions for the solution of the system of differential equations above are constituted by the value of pressure at the end of the pipe where the flow rate transient is applied, just before its application:

$$p(t, 0) = p_o,  \quad (13)$$

and by the evolution of flow rate during the transient:

$$Q(t, 0) = \begin{cases} Q_o & \text{for } t \leq 0 \\ f(t) & \text{for } 0 < t \leq \Delta T_{trans} \\ 0 & \text{for } t > \Delta T_{trans} \end{cases} \quad (14)$$

The system of differential equations may be numerically solved using the method of characteristics (as described, e.g., in L. Debnath, Nonlinear Partial Differential Equations for Scientists and Engineers, Birkhäuser, Boston, 1997).

In addition to the pipe geometry, its discretization and the boundary and initial conditions, the following data must be fed as input to the simulator:

the time step dt of the simulation, defined by the formula $dt = \delta t/2$;

the total time $t_{sym}$ to simulate the evolution of the flow rate;

the flow rate during the transient, discretized in time with the simulation time step. For a transient represented by the complete closing of a valve, this may be:

$$Q(n\,dt, 0) = \begin{cases} Q_o & \text{for } n = 0 \\ \text{evolving from } Q_o \text{ to } 0 & \text{for } n = 0 \ldots \Delta T_{trans}/dt \\ 0 & \text{for } t < \Delta T_{trans} \end{cases} \quad (15)$$

where $\Delta T_{trans}$ is the time required to completely close the valve;

The speed c of propagation of the pressure waves in the liquid which, in the method of characteristics, is assumed to be constant along the pipe.

An estimate of diameter and roughness of the pipe for a length $\zeta$ from the end where the transient is applied. The value of $\zeta$ may be computed from the speed of sound, the time interval of the transient $\Delta T_{trans}$ and the time interval to the inflection point of the measured pressure curve $\Delta T_{inflex}$ (defined in FIG. 2) by using the formula:

$$\zeta = c(\Delta T_{trans} + \Delta T_{inflex}). \quad (16)$$

In fact, the characteristics of this part of the pipe, and the corresponding pressure losses, cannot be obtained by the application of the method of the present invention.

A density profile $\rho(z)$ and a viscosity profile $\mu(z)$ of the fluid along the pipe, before the transient, providing one value for each element $E_n$ constituting the pipe:

$$\rho_n = \rho(z_n) \quad (17)$$

$$\mu_n = \mu(z_n) \quad (18)$$

the value of pressure at time 0, just before the transient, at the end of the pipe where the transient is applied:

$$THP(t=0) \quad (19)$$

corresponding to the flow rate $Q_o$.

As an output from the simulator, one obtains:

the evolution in time of the fluid velocity along the pipe $v^{up}_n(j\,dt)$ and $v^{down}_n(j\,dt)$ with $j=0 \ldots t_{sym}/dt$ the evolution in time of the average pressure $p_n(j\,dt)$, with $j=0 \ldots t_{sym}/dt$, of each element $E_n$ and, in particular, the evolution of the pressure at the point where the transient is applied $p_1(j\,dt) = THP(j\,dt)$.

DESCRIPTION OF THE METHOD

In the following, the steps necessary for the application of the method of the present invention are described. For the sake of clarity, the method will be described in the case of a petroleum production well. It is nevertheless to be understood that the method is applicable to any pipe transporting a liquid.

1) Generation and Measurement of a Pressure Transient

The pressure transients necessary for the application of the method are induced by flow rate changes. The latter are preferably generated by complete closures of a valve localized at one end of the pipe, but can be generated also by partial openings or closures of such valve. If the outlet pressure of the pipe (THP) is lower than the bubble pressure of the fluid, so that free gas is present in the pipe, it is necessary to increase the pressure in the pipe above the bubble pressure. In a well, this might be obtained by choking the production flow rate.

The valve may be operated manually or by a mechanical device.

The characteristic times of the transients related to the application of the method are reported in FIG. 2, where the evolution of the well head pressure during a complete closure of a valve is shown.

Pressure data must be sampled and recorded starting before the generation of the transient (t=0) and for a time $t_{max}$; greater the time necessary for the pressure wave to reach the other end of the pipe and return back. As a rule of thumb, for each kilometer of pipe length, approximately two seconds of pressure signal recording are necessary. More precisely, if c is the speed of propagation of the pressure wave in the pipe and L is the length of the pipe under inspection, the following inequality must hold: $t_{max} > 2L/c$. We indicate with $\delta t$ the time interval between sampled pressure values $$THP(t) \; t=0, \delta t, 2\delta t, \ldots, t_{max}.$$

The recorded pressure values are necessary for the successive steps of the method.

2) Interpolation of the Flow Rate Transient

In this step, the THP sampled values are processed in order to obtain the evolution Q(t) of flow rate during the transient: starting from a guess value Q(t=0) and using an appropriate functional form (e.g. a sequence of $2^{nd}$ degree polynomials), by a history match of sampled THP values with respect to the simulated ones, the values of Q(n dt) during the transient is derived. For a complete closing, the guess value Q(t=0) must be adapted so that, after the end of the transient, the interpolated flow rate value is zero.

3) Computation of the Diameter (or Roughness) Profile Along the Pipe

This is the main step of the method. Applying the pressure values sampled in Step 1 and the flow rate change derived in Step 2, the diameter profile D(z) (or roughness profile $\epsilon(z)$) along the pipe is obtained by a history match of the simulated THP with respect to the measured one in the time interval successive to the completion of the flow rate transient.

In practice, starting from the element $E_k$, with $k=\zeta/\lambda=(\Delta T_{trans}+\Delta T_{inflex})/dt$, the value of diameter $D^{down}_k$ is adjusted in order to fit the THP simulated to the measured one at time $\Delta T_{trans}+j \; dt$:

$$THP_{sym}(\Delta T_{trans}+j \; dt)=THP_{measured}(\Delta T_{trans}+ j \; dt) \; j=1, \ldots$$

This is performed until all the diameter (roughness) values along the pipe are adjusted.

In this way, in a single run, all the diameters of the elements of the pipe are obtained from the pressure values measured at one end of the pipe during the pressure wave propagation to the other end of the pipe an back.

4) Computation of the Pressure Drop Profile at a Given Flow Rate

This step is necessary because the measurements performed at different times on the pipe often correspond to different operating flow rates $Q_o$. Yet, the comparison of pressure drops along the pipe must be performed under identical flow conditions in order to correctly estimate the pipe properties under investigation. Consequently, in Step 4, the diameter (roughness) profile obtained in Step 3 is used in order to compute the wall friction profile along the pipe at a given steady reference flow rate, appropriate to the case under investigation. The wall friction profile obtained in Step 4 may be directly compared to the profiles obtained in previous or later applications of the method of the present invention, thus revealing, e.g. the build-up of deposits in the pipe.

In practice, using the equation of the steady pressure drop applied to determine the initial conditions for the solution of the system of differential equations, a pressure drop $\Delta p_n$ is computed for each element $E_n$ at the reference steady flow rate. The profile $\Delta p_n$ may be directly superimposed to previous and later profiles to detect and localize changes in the internal state of the pipe.

EXAMPLE

An example of the application of the method of the present invention is reported for an Italian petroleum well. In Step 1 a complete closure of a well head valve has been performed, while measuring the THP values shown in FIG. 1. The THP data have been processed as in Step 2, thus obtaining the flow rate evolution shown in FIG. 3. Then the THP data have been used as in Step 3 and the history match result is shown in FIG. 4. The diameter profile corresponding to the history match is shown in FIG. 5. Applying Step 4 of the method, two measurements performed respectively before and after a solvent cleaning job of the deposits present in the well could be compared directly, as show in FIG. 6. The method of the present invention has thus allowed to localize the deposits removed by the solvent through the analysis of well head pressure data collected during two complete closures of the well of 20 s each. The very short duration of the closures implies very little costs of the measurement and the risk associated to the use of down hole tool has been completely avoided.

FIGURES

FIG. 1: Step 1 of the method. Sampled values of the tubing head pressure (THP) along time. The measurement has been performed on a vertical well with a change in diameter localized at about 1680 m depth. Corresponding to the diameter change, a step in pressure is observed after about 4 s since the generation of the transient.

FIG. 2: Step 1 of the method. First part of the evolution of the THP in time after the generation of the pressure transient. The various time intervals relevant to the method of the present invention are illustrated.

FIG. 3: Step 2 of the method. Interpolated evolution of the flow rate during the generation of the pressure transient.

FIG. 4. Step 3 of the method. History match of the measured THP and the simulated one, obtained by adjusting the diameter profile along the pipe.

FIG. 5. Step 3 of the method. Diameter profile along the well which enables the simulator to reproduce the measured THP data.

FIG. 6. Step 4 of the method. Pressure losses per unit length [bar/m] along the well tubing obtained at the reference flow rate of 10 m³/h. The two curves shown have been obtained respectively before and after a solvent wash which has removed the deposits present in the pipe, thus enabling the localization of said deposits in the depth zone between 3400 and 5600 m.

The invention claimed is:

1. Method for the determination of the friction pressure drops along any pipe transporting liquids, the discharge pressure of said pipe being higher than the bubble pressure of the transported liquids, comprising:
   (a) a first Stage of measure in time of the pressure transients generated by flow rate changes;
   (b) a second Stage of processing of pressure data acquired in Stage (a), thus obtaining the evolution of the flow rate in the pipe during the transient;
   (c) a third Stage of processing of the pressure data acquired in Stage (a) in which, making use of the evolution of flow rate determined in Stage (b), the diameter or roughness profile along the pipe is derived;
   (d) a fourth Stage in which the diameter or roughness profile obtained in Stage (c) is used to compute the wall friction profile along the pipe at any given steady flow rate.

2. Method as in claim 1 in which the liquids transported in the pipe are related to the petroleum industry.

3. Method as in claim 1 in which the pipe is located in a petroleum industry well.

4. Method as in claim 1 in which the pipe can be arranged vertically, horizontally or along any geometric profile.

5. Method as in claim 1 characterized by the fact that the flow rate changes are induces by fast and complete closures of a valve localized at one end of the pipe.

6. Method as in claim 1 characterized by the fact that the valve closures are operated by a dedicated valve actuator device.

7. Method as in claim 1 characterized by the fact that in Stage (a) the flow rate transient is completed in less than 0.5 s and the pressure sampling frequency is higher than 20 Hz.

* * * * *